United States Patent [19]

Bengmark

[11] Patent Number: 4,887,996

[45] Date of Patent: Dec. 19, 1989

[54] METHOD AND TUBE EQUIPMENT FOR SUPPLYING FLUID TO A SPACE AND DRAINING SAID SPACE

[76] Inventor: Stig Bengmark, Box 5121, S-220 05 Lund, Sweden

[21] Appl. No.: 90,484

[22] Filed: Aug. 28, 1987

[30] Foreign Application Priority Data

Feb. 13, 1987 [SE] Sweden .................. 8700582

[51] Int. Cl.⁴ .................................... A61M 25/00
[52] U.S. Cl. ................................ 604/54; 604/281
[58] Field of Search .................. 604/54.8, 281

[56] References Cited

U.S. PATENT DOCUMENTS

| 4,169,464 | 10/1979 | Obrez | 604/281 |
| 4,307,723 | 12/1981 | Finney | 604/281 |
| 4,531,933 | 7/1985 | Norton et al. | 604/281 |
| 4,568,338 | 2/1986 | Todd | 604/281 |
| 4,694,838 | 9/1987 | Wijayarthna | 604/281 |

FOREIGN PATENT DOCUMENTS

| 1508018 | 1/1967 | France . |
| 155913 | 6/1983 | Norway . |
| 193885 | 6/1957 | Sweden . |

*Primary Examiner*—Stephen C. Pellegrino
*Attorney, Agent, or Firm*—Beveridge, DeGrandi & Weilacher

[57] ABSTRACT

A space communicating with the atmosphere via a cavity and a passage is supplied with a fluid or drained by means of a tube made of a flexible elastic material and having a tendency to coil up. Upon insertion into said space, the tube is first held in a straightened-out condition by means of a guide of flexible but unelastic material which is introduced into said tube and then withdrawn therefrom to permit the tube to coil up within the cavity and to be conveyed into the space by a substance supplied to the cavity. The method can be used advantageously for supplying a drug or nutriment directly to the intestine by conducting the tube in its straightened-out condition through the nose, the throat and the gullet down into the stomach where it is allowed to coil up in order to be transported into the intestine by normal ingestion of the food.

The tube employed for carrying the method into effect consists of a flexible plastic or rubber material and tends to coil up with a predetermined force, the guide consisting of flexible but unelastic material and tending to straighten itself out with a force exceeding the coiling-up force of the tube.

1 Claim, 1 Drawing Sheet

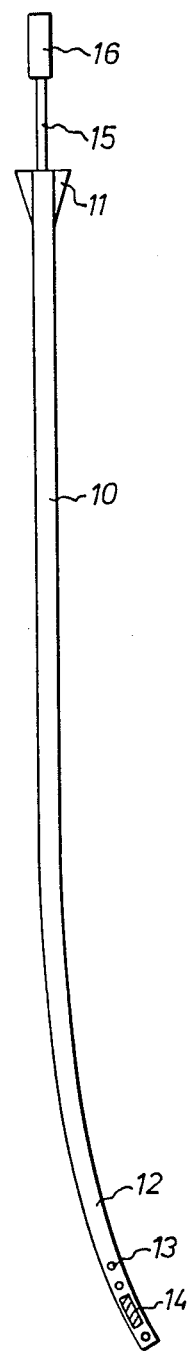
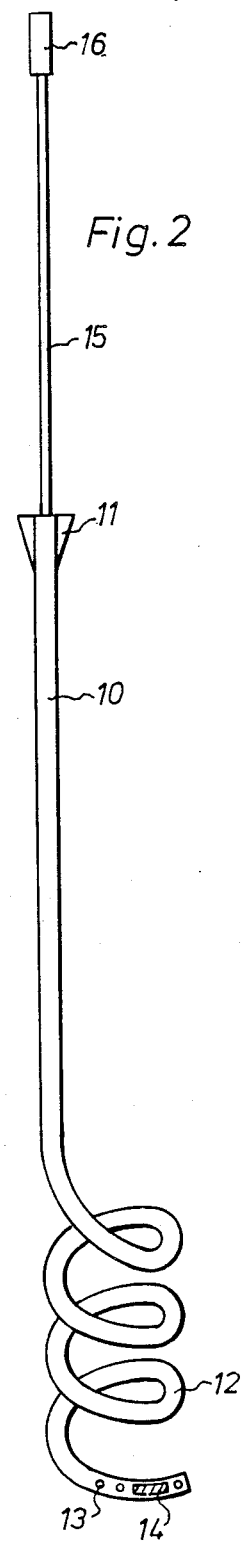

4,887,996

METHOD AND TUBE EQUIPMENT FOR SUPPLYING FLUID TO A SPACE AND DRAINING SAID SPACE

BACKGROUND OF THE INVENTION

The present invention relates to a method for supplying fluid to a space in a fluid transport system, or for draining said space which is located downstream of a cavity having an inlet and an outlet.

There are occasions when it is desired to bypass a cavity of this kind, for example by means of a tube from the inlet to the outlet, and if the inlet of the cavity is not in alignment with the outlet, difficulties occur. In such cases, one must use a tube which is sufficiently rigid and "feel one's way" to the outlet, and this is frequently inadvisable or impossible.

It has been tried in various ways to form the tube end portion in such a manner that it accompanies the fluid passing through the cavity from the inlet to the outlet, but without much success. Cavities of this type are to be found in a variety of applications, but one specific and obvious cavity is the human stomach which occasionally must be bypassed for fluid supply directly to the intestine. The background for this is as follows. After a major operation, especially in the abdomen, the stomach is temporarily paralysed for a few days, and the patient has difficulty in eating and keeping his food down. As a result, the supply of nutriment via the stomach is replaced by intravenous ingestion. However, this technique suffers from a number of shortcomings and necessitates the use of sterile solutions which will be expensive because they can be supplied only by trained nurses. In addition, the veins frequently become inflamed locally, and other changes may be caused by the inactivity of the intestine. It will thus be obvious that there are several reasons for postoperative supply of nutriment via the intestine. It is generally considered among surgeons that the postoperative supply of nutriment via the intestine (enteral supply) will gain ground in the next decade.

It is, however, no easy matter to pass a catheter past the stomach to the small intestine. It has been tried to use a catheter to which a balloon was affixed, and on the balloon mercury was deposited. This catheter which is termed the Miller-Abbot catheter, is used very restrictively, inter alia because of the risk of mercury leakage. The catheters that are available on the market suffer from the disadvantage that X-ray technique is required to be able to pass the catheter past the stomach and down into the intestine.

SUMMARY OF THE INVENTION

Initially, it was the object of the invention to solve the last-mentioned problem in a simple and feasible manner. However, since similar problems occur in other applications, both medical and purely technical applications, the main object became to provide a more generic solution. The solution that was finally developed, is characterised by a predetermined length of a tube of a flexible elastic material having an inherent tendency to coil up along at least said predetermined length in a specific pattern, a so-called programmed catheter. The catheter is passed into the cavity via the inlet by means of a guide inserted in the tube and made from flexible but unelastic material, said guide tending to straighten itself in the unactuated state with a force exceeding the force of the coiling-up tendency of the tube, such that, upon withdrawl of the guide from the tube, the tube can coil up within the cavity until a substance supplied to the cavity straightens the tube and transports it to the said space via the cavity outlet in order to supply or take up fluid within said space.

In this manner, not only nutriments, but also drugs can be administered directly to the intestine, the cavity being formed by the stomach of a patient, and the inlet of the cavity being formed by the nose, the throat and the gullet, the small intestine constituting the said space. After the tube length has been passed down into the stomach and coiled up, the ingestion of food takes place in the normal manner for a predetermined period of time during which the coiled-up tube length is transported into the intestine by the processed food and the stomach movements. The intestine perceives the coiled-up (programmed) tube length as food, and the peristalsis of the intestine passes the tube length further down. In this manner, the catheter has imparted to it the unique property of being self-feeding.

A tube equipment for such supply of fluid or for draining is characterised in that it comprises a flexible and elastic, plastic or rubber material, for example silicone rubber, which has in its unactuated state and along at least a part of its length a coiling-up tendency, and a guide insertable into the tube and consisting of a flexible but unelastic material, for example a steel wire which, in its unactuated state, tends to straighten itself with a force exceeding the coiling-up force of the tube, the guide after insertion in the tube maintaining said tube in a straightened-out state for insertion in a cavity via a passage and permitting, after withdrawal, coiling-up of the tube length within said cavity.

BRIEF DESCRIPTION OF THE DRAWINGS

The invention will be described in more detail below, reference being had to the accompanying drawing, which is an elevational view of the tube equipment according to the invention, FIG. 1 showing a guide inserted in the tube and FIG. 2 showing the guide partly withdrawn.

DETAILED DESCRIPTION

FIG. 1 shows a tube 10 of flexible and elastic, plastic material, preferably silicone rubber. The tube may be manufactured in conventional manner, but before the material has finally hardened, the tube is coiled up on a core of suitable cross-section and is finally hardened in this condition. After the core has been removed, the tube will thus tend to coil up. The coiling-up tendency can be imparted to the tube also in other ways, for example by selecting a suitable material, or by subsequent heating and curing on a core. At one end, the tube 10 has a widened portion or lugs 11 providing a firm hold on the tube, and the tube end can be affixed in a suitable holder. At its opposite end 12, the tube may be perforated, as shown at 13, and furthermore it may be provided with a means 14 traceable by X-ray technique. The tube 10 preferably is manufactured in large lengths which are then cut into suitable pieces which are provided with lugs 11 and, if required, perforations 13 and an X-ray contrast agent 14 which may consist of a material inserted in the tube wall or affixed thereto, such as a thin metal piece.

Inserted in the tube 10 is a guide 15 which consists of a flexible but unelastic, relatively rigid material, preferably a stranded steel wire. A guide 15 has at one end a handle-like portion 16 to facilitate insertion of the guide 15 in the tube and its withdrawal therefrom. The guide 15 has a length which corresponds to or is slightly shorter than the length of the tube 10. The guide also has a tendency to straighten itself with a force exceeding the coiling-up force of the tube.

In its unactuated state, the tube 10 is coiled up in the manner illustrated in FIG. 2, but is straightened out by insertion of the guide 15, as shown in FIG. 1.

For the primary object of the invention, which is the supply of nutriment directly to the intestine following an operation, one proceeds as follows. Some time before the operation, for example one or two days, the tube 10 with the guide 15 inserted therein is passed through the patient's nose, throat and gullet until the lower tube end 12 enters the stomach. Care must be taken that the tube will extend all the way from the gullet through the stomach and enter the small intestine with an end portion. For this purpose, it may be necessary to withdraw the guide 15 a distance such that the outer tube end will coil up, whereupon a further length of tube is passed down into the stomach. After that, the guide is withdrawn in its entirety, and the outer tube end is fixed by some suitable means. The patient now can ingest in the normal way. The food which enters the stomach surrounds the coiled-up tube end which is now processed by the stomach in the same manner as the food and is passed together with the food into the small intestine, after it has been straightened, and is retained therein. The position of the tube end is readily checked by X-ray technique. The patient is now operated upon, and after the operation nutriment can be readily administered to the patient. To facilitate the administration of nutriment in the intestine, the tube end can have the perforations 13 shown in FIG. 1.

As already mentioned, the invention can be used for many other applications, such as the administration of drugs directly into the intestine when the stomach does not tolerate the drug in question. Furthermore, it is possible to use the tube according to the invention for draining, and besides the medical application, the tube can be used in fluid transport systems where a direct communication between a space beyond a cavity is desired. The tube 10 shown in the drawing has such dimensions, that, after it has been positioned in the gullet, it does not prevent normal ingestion of food. However, its dimensions can be reduced to such an extent that the tube can be inserted in a vein. For technical applications, far larger dimensions are selected.

What I claim and desire to secure by Letters Patent is:

1. A method of positioning a catheter in the small intestine of a patient, said catheter including a flexible elastic tube having an inlet and an outlet, said catheter having a coiling portion which has an inherent tendency to coil up, said method including the steps of inserting a guide into the catheter to straighten up said coiling portion, inserting the catheter and guide into the patient to a position where the coiling portion is in the patient's stomach, removing the guide from the catheter so that the coiling portion of the catheter becomes coiled within the stomach, and subjecting the catheter and processed food within the stomach to peristaltic action to carry the coiling portion into the small intestine and uncoil it.

* * * * *